US00PP25362P3

(12) United States Plant Patent
Thome

(10) Patent No.: US PP25,362 P3
(45) Date of Patent: Mar. 24, 2015

(54) APPLE TREE NAMED 'THOME RED'

(50) Latin Name: *Malus domestica*
Varietal Denomination: Thome Red

(71) Applicant: International Plant Management, Inc., Lawrence, MI (US)

(72) Inventor: Steven J Thome, Comstock Park, MI (US)

( * ) Notice: Subject to any disclaimer, the term of this patent is extended or adjusted under 35 U.S.C. 154(b) by 110 days.

(21) Appl. No.: 13/694,906

(22) Filed: Jan. 22, 2013

(65) Prior Publication Data

US 2014/0208466 P1 Jul. 24, 2014

(51) Int. Cl.
*A01H 5/00* (2006.01)

(52) U.S. Cl.
USPC ..... Plt./161

(58) Field of Classification Search
USPC ..... Plt./161, 172
See application file for complete search history.

*Primary Examiner* — Kent L Bell

(57) ABSTRACT

A new and distinct variety of McIntosh apple tree, 'Thome Red,' originating as a naturally occurring limb mutation of the *Malus domestica* variety of 'Caudle' (U.S. Plant Pat. No. 9,068). This new variety is unique from its parent in the early timing of the red coloration the skin of the fruit, a much redder coloration of the skin of the fruit at maturity and the red coloration of the leaf petiole and veins.

3 Drawing Sheets

*Malus domestica.*

DESCRIPTION OF RELATED APPLICATIONS

The new variety, 'Thome Red' differs from its parent, 'Caudle' (U.S. Plant Pat. No. 9,068), and other varieties in the following characteristics:

A. The fruit of the new variety differs from all other varieties known to the inventor in that it is a mutation of Caudle' (U.S. Plant Pat. No. 9,068).

B. The new variety differs from its parent, Caudle' (U.S. Plant Pat. No. 9,068) in that it show bright red coloration 7 to 8 weeks earlier than its parent and finishes to a much fuller, brighter, red coloration at maturity.

BACKGROUND OF THE INVENTION

A new and distinct variety of apple tree originating as a naturally occurring limb mutation of the *Malus domestica* variety of 'Caudle' (U.S. Plant Pat. No. 9,068), hereinafter referred to as the 'Thome Red'. This new sport is unique from its parent because the fruit starts coloring in early July. The color finishes to a virtually 100% solid, red color with wide stripes. The new variety also exhibits darker coloration of the leaf petiole than the parent.

SUMMARY OF THE INVENTION

This new and distinct variety of apple tree was discovered in 2003 as a limb mutation of 'Caudle' (U.S. Plant Pat. No. 9,068), in an orchard planted in 2000 on Mailing 9 (NAKB 337), (an unpatented selection) rootstock. The new variety was noticed because the fruit started coloring in early July to a bright red finish. This coloration was observed because at that time the fruits on the parent tree were still green in color.

Observations during the next four seasons confirmed that the fruit started coloring in early July to a bright red finish with a bold red stripe, as opposed to 'Caudle' (U.S. Plant Pat. No. 9,068), which colors at maturity to a red striping over a greenish-yellow background. The mature fruit of the new variety finishes to a full red coloration with a bold red stripe. The new variety also exhibits a red coloration of the leaf petiole and veins. To summarize, the new invention differs from "Caudle", its closest comparison, in that it starts fruit coloration earlier, finishes to a much redder color with more prominent striping than "Caudle", and exhibits red coloration of the leaf petiole and veins compared to "Caudle" which has green petioles and vein coloration.

In August of 2003, buds were taken from the original limb and trees for further testing were produced by chip budding on Mailing 9 (NAKB 337) (an unpatented selection) rootstock in Brentwood, Calif. The new variety has remained true to the description herein contained. The new variety has not been grown on its own root.

DESCRIPTION OF THE DRAWINGS

The accompanying photographs show typical specimens of the new variety as depicted in color as nearly true as is reasonably possible in color illustrations of this character. These specimens were obtained at Kent County, Mich.

DETAILED BOTANICAL DESCRIPTION

Figure 1:
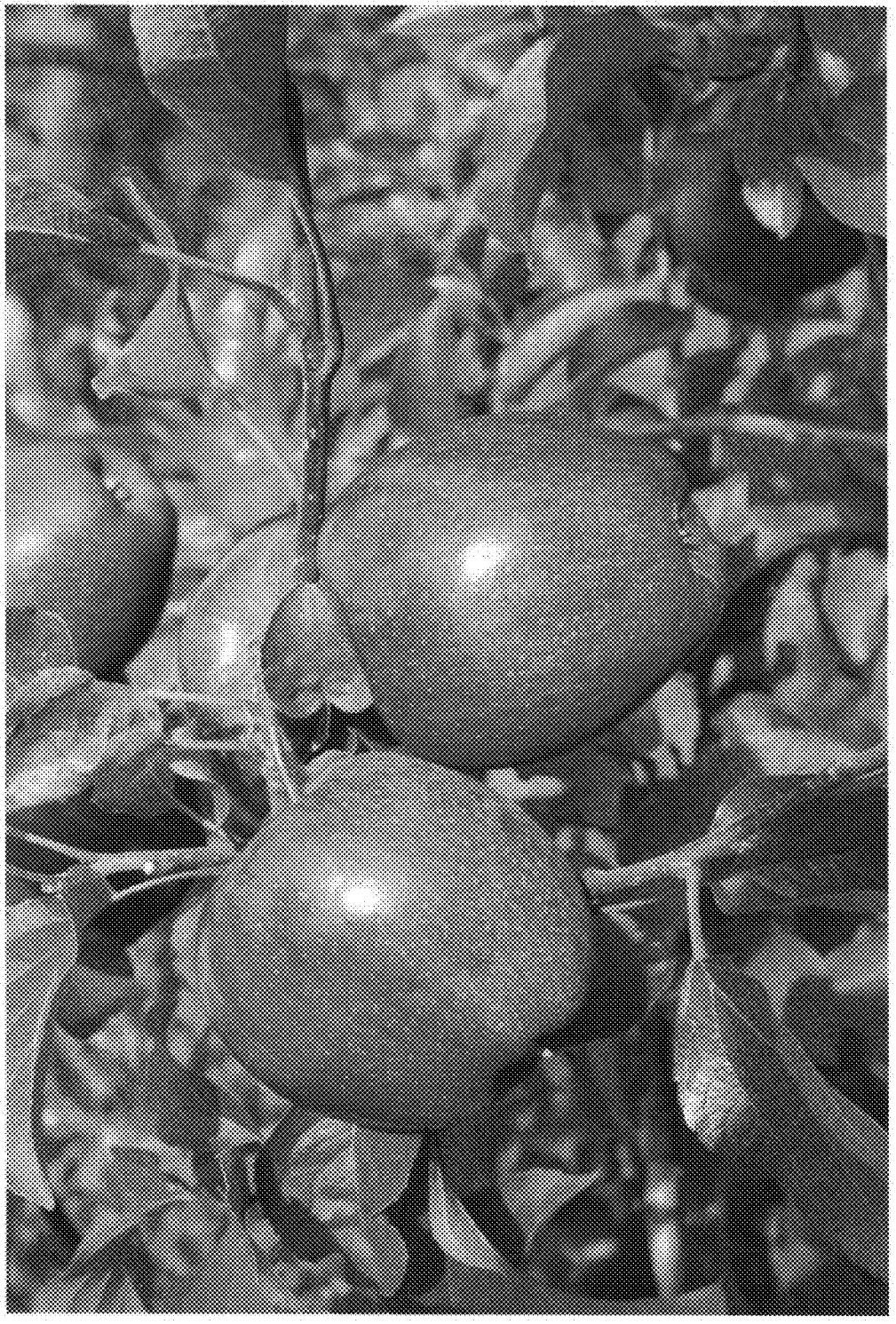
FIG. 1 illustrates the fruits and foliage of the new variety at maturity showing the intense coloring of the new variety and the red coloration of the leaf petiole.
Figure 2:
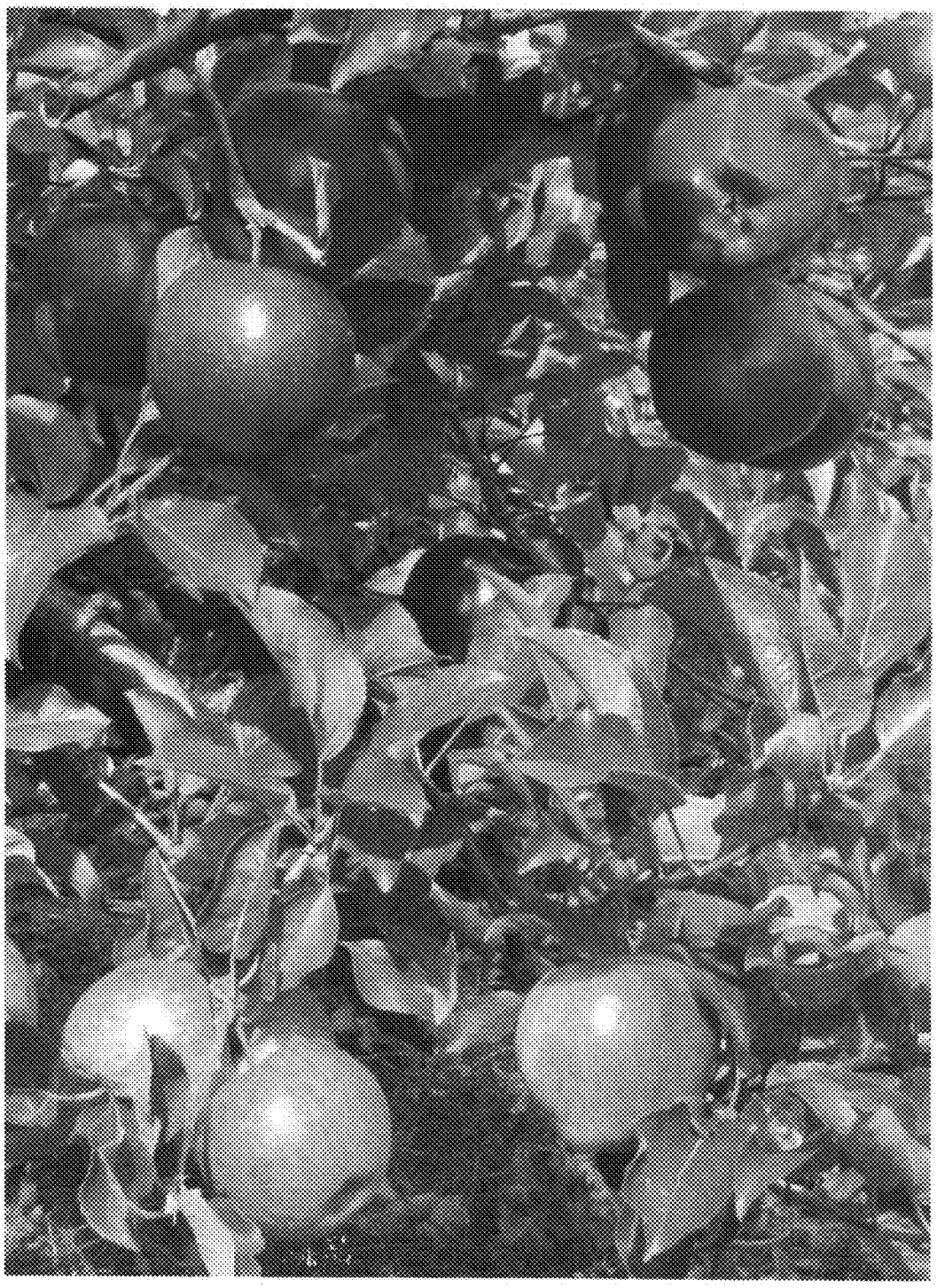
FIG. 2 illustrates original tree with the new variety on the top and the parent 'Caudle' (U.S. Plant Pat. No. 9,068), on the bottom at maturity, showing the differences in the mature coloration of the fruit.
Figure 3:
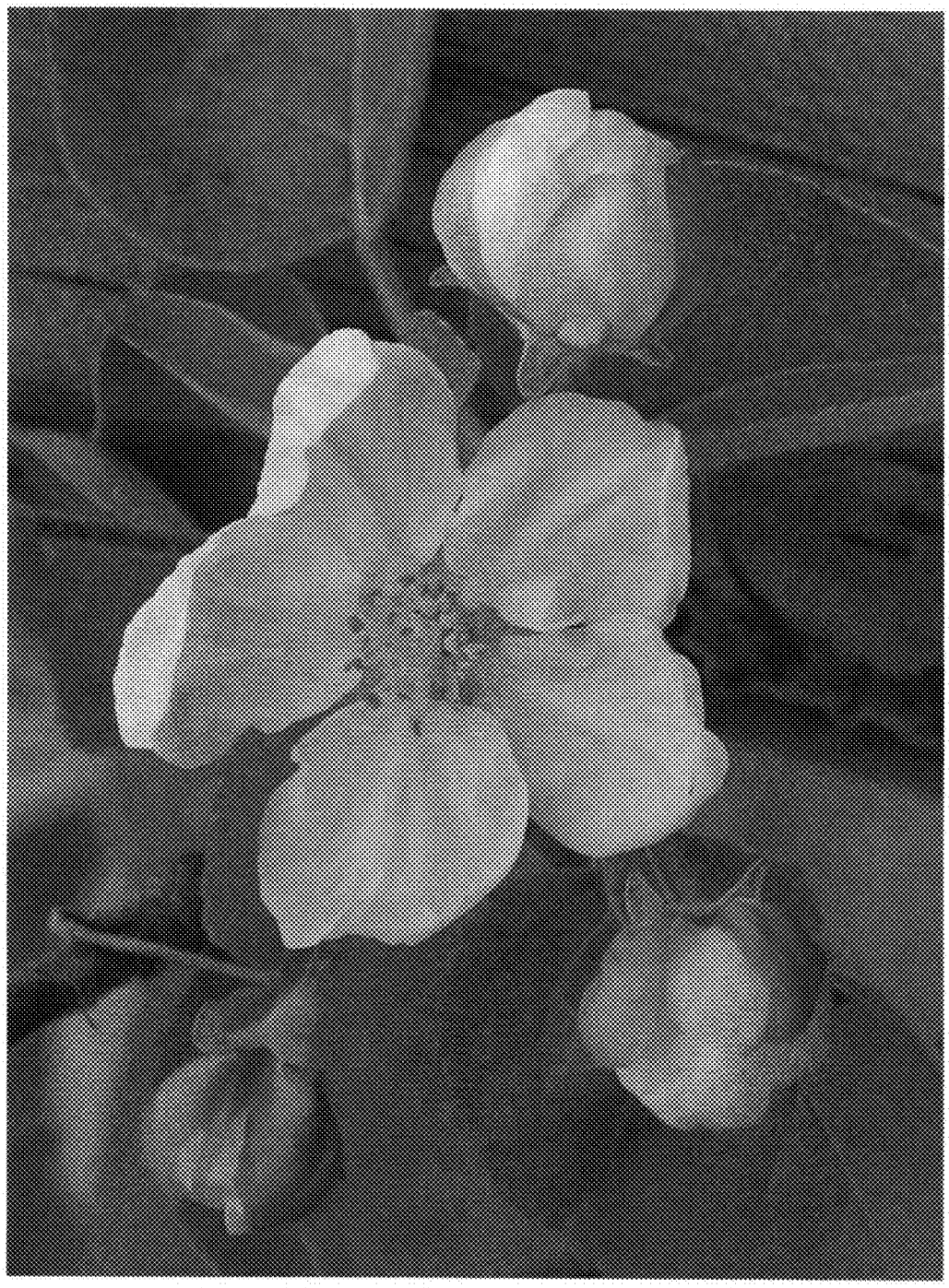
FIG. 3 illustrates a blossom and buds of the new variety.

A detailed description of the 'Thome Red' cultivar follows using The Royal Horticultural Society of London Colour Chart, 1986 edition, for color identification except where general color terms are sufficient.

Parentage: A naturally occurring limb mutation of 'Caudle' (U.S. Plant Pat. No. 9,068). Locality of the original discovery and observations is Kent County, Mich.

Tree:

*Age.*—8 years.

*Size.*—Large, height 3 m, width 2 m.

*Vigor.*—Vigorous, yearly growth averages 0.5 m.

*Density.*—Open.

*Form.*—Spreading, somewhat weeping.

*Production.*—Very productive, averaging 800 bushels per acre.

*Growth type.*—Non-spur.

*Bearing.*—Annual.

Trunk:

*Size.*—8 cm in diameter at 40 cm above ground level.

*Surface.*—Smooth.

*Bark color.*—Gray 201B.

*Lenticels.*—Length 1 to 3 mm, width 0.05 mm.

*Lenticel color.*—Grayed Green 198C.

*Lenticel density.*—2 to 3 per $cm^2$.

Branches:

3 *year old branch.*—30 mm in diameter, color Grey 201B, angle to 4 year old branch 90°.

2 *year old branch.*—20 mm to 30 mm in diameter, length 24 cm to 30 cm, color Grey 201B, angle to 3 year old branch 35° to 45°.

1 *year old branch.*—5 mm to 8 mm in diameter, length 20 cm to 35 cm, color Grayed Orange 177A, angle to 2 year old branch 30° to 45°; lenticels 0.05 mm in diameter, round, color Grayed White 156C.

Leaves:

*Size.*—Length 120 mm, width 65 mm.

*Texture.*—Leathery, crisp.

*Form.*—Broadly ovate.

*Base.*—Broadly cuneate.

*Apex.*—Acute.

*Margin.*—Serrate.

*Adaxial surface pubescence.*—Absent.

*Abaxial pubescence.*—Very fine.

*Adaxial surface color.*—Green 147A.

*Abaxial surface color.*—Green 138B.

*Venation.*—Pinnate, 10 to 12 veins, mainly alternate, mid-vein color Red Purple 59A, secondary veins starting with Red Purple 59A at mid-vein, bleeding to Red Purple 58C to Green 138B at leaf margin.

*Petiole length.*—35 mm to 40 mm.

*Petiole width.*—3 mm at abscission layer to 1.5 mm to 2 mm at junction with leaf.

*Petiole adaxial color.*—Grayed Orange 177A.

*Petiole abaxial color.*—Red Purple 59A.

*Petiole groove.*—Extremely shallow, 0.01 mm in depth.

*Stipules.*—None observed.

*Leaf glands.*—None observed.

Leaf buds:

*Length.*—6 mm.

*Width.*—3 mm.

*Color.*—Grayed Purple 184A.

*Placement on branch.*—Alternate.

*Internode distance.*—15 mm to 25 mm.

Spurs: Present on 1 year and older wood.

*Length.*—6 mm.

*Width.*—5 mm.

*Color.*—Grayed Purple 184A.

Flowers:

*Bloom period.*—7 to 10 days dependent on temperature and other weather factors.

*Bloom timing.*—Late mid-season.

*Presentation.*—Very showy.

*Fragrance.*—Faint.

*Pollen.*—Present.

*Fertility.*—Fertile, will pollinate itself and any other late mid-season blooming varieties such as "Jonathan" (an unpatented selection) or "Rome" (an unpatented selection).

*Pollination requirements.*—Will set better and more uniform crops with pollen from other late mid-season blooming, fertile varieties such as "Jonathan" (an unpatented selection) or "Rome" (an unpatented selection).

Flowers at popcorn stage:

*Pedicel.*—Length 3 cm, diameter 0.2 mm.

*Pedicel color.*—Green 139D.

*Bud.*—Length 9 mm, width 9 mm, shape round.

*Bud color.*—Red Purple 64C on outer surface of petals, inner surface is White 155D.

Flowers at full bloom:

*Corolla diameter.*—3 cm.

*Numbers of flowers per cluster.*—5 to 7.

Petals:

*Arrangement.*—5 in number, length 1.5 cm to 2 cm, width 1 cm.

*Color.*—Upper surface: White 155D. Lower surface: White 155D with a blush of Red Purple 62B.

*Base.*—Blunt with sharply pointed attachment to peduncle.

*Shape.*—Broad, pointed at tip and apex, edges and tip curled inward, petals slightly overlapping.

*Margins.*—Slightly rippled with an occasional notch.

*Texture.*—Soft.

*Peduncle.*—Length 11 mm, width 1 mm, color Green 139D.

*Pedicel.*—Length 35 mm, width, 0.3 mm, color Green 139D.

*Sepals.*—Pointed with slight recurve, 5 in number, length 0.5 mm, width 1 mm, Upper and lower surfaces color Green 139D.

*Stamens.*—20 to 23 in number, color White 155D.

*Anthers.*—Oblong in shape, size 0.01 to 0.05 mm. color Yellow 13A.

*Pistil.*—Held at same height as anthers in a majority of blossoms, length 2 mm.

*Ovary.*—Length 0.2 mm, width 0.1 mm, color Green 138D, pubescent. Style: length 0.2 mm, width 0.01 mm, color Green 139B. Stigma: length 0.01 mm, width 0.05 mm, color Yellow 13B.

Fruit:

*Maturity when described.*—Firm ripe.

*Date of picking.*—October 22, in Kent County, Mich.; generally harvested in one picking.

*Size.*—Axial diameter 96 mm, transverse diameter 80 mm.

*Fruit weight* (*firm ripe*).—275 g.

*Form.*—Uniform, symmetrical, regular, oblong to conical.

*Cavity.*—Acuminate, depth 20 mm, width 25 mm.

*Basin.*—Symmetrical, acute at base, narrow, depth, 18 mm, width 10 mm.

*Calyx.*—Open, segments persistent, recurved, outer and inner surfaces pubescent.

Skin:

*Thickness*.—Medium.

*Texture*.—Smooth, medium cuticle wax.

*Tendency to crack*.—Slight.

*Lenticels*.—Color Orange White 159D, round, prominent, length 0.2 mm. width 0.2 mm, 2 to 3 per $cm^2$.

*Color*.—Background color Red Purple 59A with stripes of Red 53B and Red Purple 60A.

Flesh:

*Aroma*.—Sweet, aromatic.

*Firmness*.—Very firm, averaging 17 to 20 pounds pressure.

*Texture*.—Firm, tender, fine, crisp.

*Eating quality*.—Best.

*Soluble solids*.—12.4 to 12.5 brix.

*Starch*.—6.1, (42% flesh staining).

Core:

*Bundle area*.—Medium to ovate in shape, symmetrical at base.

*Bundles*.—5 in number, inconspicuous, green, alternate above stamens.

*Carpillary area*.—Distinct, medium size.

*Calyx tube*.—Urn shaped, open.

*Depth of tube to shoulder*.—18 mm.

*Styles*.—Distinct, pubescent.

*Stamens*.—One distinct whorl, small, Yellow Green 144C.

*Locules*.—Walls thin, tough, length 10 mm, width 5 mm.

*Longitudinal section*.—Broadly ovate.

Seeds:

*Number perfect*.—8 to 12.

*Number in one cell*.—2 to 4.

*Length*.—10 mm.

*Width*.—6 mm.

*Form*.—Obtuse, non-tufted.

*Color*.—Grayed Orange 166A.

Stem:

*Length*.—30 mm.

*Width*.—2.5 mm at base to 4 mm at end.

*Color*.—Grayed Orange 165A.

Use: Processing, fresh market, dessert.

Shipping quality: Excellent.

Keeping quality: Excellent, 90 to 120 days in common storage, 6 months in common storage, 6 months in controlled atmosphere storage.

Tree winter hardiness: Average for an apple variety. Tree is hardy to −10° to −25° F.

Bud winter hardiness: −15° to −20° F., dependent on the stage of development of the bud.

Drought tolerance: Average for an apple tree. Normal requirements average ½" of rain per week. Severe drought adversely affects fruit size and quality.

Disease resistance: Susceptible to fire blight (*Erwinia amylovora*) and other bacterial.

Diseases: Moderately susceptible to apple scab (*Venturia inaequalis*), powdery mildew (*Podosphaera leucotricha*), and other fungal diseases.

I claim:

1. A new and distinct variety of apple tree, *Malus domestica*, substantially as herein illustrated and described.

* * * * *